United States Patent [19]
Baldus et al.

[11] Patent Number: 5,453,527
[45] Date of Patent: Sep. 26, 1995

[54] SILICON-ALUMINIUM NITRIDE CERAMIC AND PRECURSOR COMPOUNDS, PROCESSES FOR THEIR PREPARATION AND THEIR USE

[75] Inventors: Hans-Peter Baldus, Burscheid; Oliver Wagner; Martin Jansen, both of Bonn, all of Germany

[73] Assignee: Bayer Aktiengesellschaft, Leverkusen, Germany

[21] Appl. No.: 160,338

[22] Filed: Dec. 1, 1993

[30] Foreign Application Priority Data

Dec. 8, 1992 [DE] Germany .......................... 42 41 287.0

[51] Int. Cl.$^6$ .............................. C07F 5/06; C04B 34/58
[52] U.S. Cl. ........................................ 556/173; 423/327.1
[58] Field of Search ......................... 556/173; 423/327.1

[56] References Cited

U.S. PATENT DOCUMENTS

| | | |
|---|---|---|
| 3,959,446 | 5/1976 | Mazdiyasni et al. . |
| 4,145,224 | 3/1979 | Mehalchick et al. . |
| 4,196,178 | 4/1980 | Iwai et al. . |
| 4,851,205 | 7/1989 | Mitomo ............................. 423/327.1 |
| 5,110,773 | 5/1992 | Corral et al. ...................... 423/327.1 X |
| 5,370,853 | 12/1994 | Schnick et al. ................... 423/327.1 X |

FOREIGN PATENT DOCUMENTS

| | | |
|---|---|---|
| 167306 | 1/1986 | European Pat. Off. . |
| 305985 | 3/1989 | European Pat. Off. . |
| 344870 | 12/1989 | European Pat. Off. . |
| 0434428 | 6/1991 | European Pat. Off. . |
| 495325 | 7/1992 | European Pat. Off. . |
| 502399 | 9/1992 | European Pat. Off. . |

OTHER PUBLICATIONS

J. Am. Cera. Soc., vol. 75 (2), pp. 259–276, 1992; "SiAlON Ceramics", T. Ekstrom et al.; + p. 2312—correction.
Journal of the American Ceramic Society, vol. 58, Nos. 7–8, pp. 346–347; "Contribution to the Phase Diagram . . . ", L. J. Gauckler et al. 1975.
Nature Physical Science, vol. 238, Jul. 10, 1972, pp. 28–29; "Ceramics based on Si–Al–O–N and Related Systems", K. H. Jack et al.
Journal of Matrials Science, vol. 11, 1976, pp. 1135–1158; "Review Sialons and related nitrogen ceramics", K. H. Jack.
Chemical Abstract, Week 8848, Refractories:Ceramics, p. 87 J6–L; 88–342946/48, J63256–594–A, "Measuring single crystal dia. in Czochralski furnace . . . ", Kyushu Denski Kinzo, Apr. 13, 1987.
Chemical Abstracts, vol. 112, No. 18, 30 Apr. 1990, Abstract No. 163709h, p. 334.
Chemical Abstracts, vol. 113, No. 20, 12 Nov. 1990, Abstract No. 183665q, p. 785.
Chemical Abstracts, vol. 115, No. 20, 18 Nov. 1991, Abstract No. 213469q, p. 355.

*Primary Examiner*—Paul F. Shaver
*Attorney, Agent, or Firm*—Sprung Horn Kramer & Woods

[57] ABSTRACT

The present invention relates to new trichlorosilylaminoalanes, new aluminosilazane compounds, new oligo or polyaluminosilazane compounds having the structural feature ≡Si—NH—Al, a silicon-aluminium nitride ceramic powder, ceramic material based on SiN and AlN, processes for the preparation of these substances and the use of the polyaluminosilazanes and of the ceramic materials.

10 Claims, No Drawings

SILICON-ALUMINIUM NITRIDE CERAMIC AND PRECURSOR COMPOUNDS, PROCESSES FOR THEIR PREPARATION AND THEIR USE

The present invention relates to new trichlorosilylaminoalanes, new aluminosilazane compounds, new oligo- or polyaluminosilazane compounds having the structural feature ≡Si—NH—Al, a silicon-aluminium nitride ceramic powder, ceramic material based on SiN and AlN, processes for the preparation of the various substances and the use of the polyaluminosilazanes and the ceramic materials.

Silicon nitride is a material which is very suitable in principle for turbochargers, turbines of jet engines, linings of rocket jets and combustion engines by virtue of its strength and corrosion resistance.

Certain properties of this material can be optimised for its subsequent uses by producing mixed ceramics. Thus JP-A 63 256 587 discloses Si/Al/N ceramic coatings which have better abrasive properties than $Si_3N_4$.

The production of structural parts from pure $Si_3N_4$ ceramic powder is very expensive and complicated. In the present state of the art, it is necessary to add oxidic sintering additives to the silicon nitride powder for complete compacting and sintering of the ceramic part. This causes amorphous glass phases to form at the grain boundaries of the silicon nitride grains, and these glass phases have an adverse effect on the high temperature strength, the corrosion resistance and the creep strength of the structural part.

In the 1970's it was discovered that $Al_2O_3$ dissolves in $\beta$-$Si_3N_4$ at high temperatures (K. H. Jack, W. J. Wilson, Nature (Phys. Sci.), 238, 28–29 (1972)). The solid solution, known as $\beta$-sialon, extends over a wide range of the $Si_3N_4$—$SiO_2$—$Al_2O_3$—AlN system (L. J. Gauckler, H. L. Lucas, G. Petzow, J. Am. Ceram. Soc., 58, 346–47 (1975)). It was found that the creep strength and corrosion resistance of densely sintered sialon ceramic were better than those of sintered silicon nitride on account of the absence or greatly reduced amount of glass phase at the grain boundaries (K. H. Jack, J. Mater. Sci., 11, 1135–58 (1976)). Moreover, sialon powder can be worked up much less expensively to a complex shaped article than $Si_3N_4$ because the sintering of sialon powder to a dense body can be achieved much more rapidly and less expensively (T. Ekström, M. Nygren, J. Am. Chem. Soc., 75[2] 259–76 (1992)).

Densely sintered sialon ceramics are generally produced by sintering a mixture of $Si_3N_4$, $Al_2O_3$ and AlN powder for about 12 hours at about 1800° C. under a nitrogen pressure of 0.1 MPa. The mixing process, however, invariably introduces impurities into the ceramic powder and these impurities are frequently the cause of breakdown of the finished ceramic part. In addition, inhomogeneities are produced by random distribution of the primary particles in spite of careful homogenisation of the starting materials and can only be broken down after prolonged sintering at high sintering temperatures.

The introduction of additional sintering additives has been avoided by absolutely homogeneous distribution of the individual elements Si, Al, N and O in the initial powder so that the introduction of impurities has also been avoided. This should have the added effect of considerably speeding up the sintering process and enable substantially lower sintering temperatures to be employed. These three factors together should on the one hand result in sialon structures with improved performance and on the other hand significantly reduce the cost of production.

In addition, homogeneous ceramic powder composed of Si, Al, N and O should also be of interest as sintering additive for sintering pure silicon nitride.

Further, ceramic powders having a homogeneous distribution of the elements Si, Al and N should lead to $Si_3N_4$/AlN- nano composites with new, interesting properties.

It is therefore an object of the present invention to provide novel organometallic precursor compounds which can be produced simply and in high yields and a process for the preparation of ceramic powders from these precursor compounds consisting of Si, Al, and N or of Si, Al, N and O and containing a total of less than 500 ppm of metals and chlorine as impurities. Completely homogeneous distribution of the participating elements should also be ensured.

These requirements are fulfilled by molecularly disperse ceramic powders, their precursor compounds, the processes for the preparation of these substances, and the use of polyaluminosilazanes and the ceramic materials as disclosed in their preferred embodiments in the Patent Claims.

It was surprisingly found that when 1,1,1-trichloro-3,3,3-trimethyl-disilazane $(CH_3)_3Si$—NH—$SiCl_3$ (A) is reacted with $AlCl_3$, two new compounds are formed, namely an μ-N,N'-bis(tri-chlorosilylamino)-bis(dichloralane) $(Cl_3Si$—NH—$AlCl_2)_2$ (I) and an μ-N,N'-bis(trichlorosilylamino)-chloralane $(Cl_3SiNH)_2AlCl$ (II). These molecular compounds are distinguished by a molecular silicon-nitrogen-aluminium bond.

The starting compound (A) can be prepared in a yield of over 90% from hexamethyldisilazane and silicon tetrachloride by stirring at room temperature. The molar ratio of hexamethyldisilazane to silicon tetrachloride is preferably from 1:10 to 4:1, most preferably about 1:2. According to the invention, crystalline (I) is obtained in 85% yield by mixing compound (A) with $AlCl_3$ in an inert organic solvent (n-hexane, toluene, ether). The molar ratios of aluminium trichloride to (A) are from 10:1 to 1:10, preferably equimolar. The reaction temperature may vary from $-100°$ C. to $100°$ C. and is preferably about $0°$ C. to $40°$ C. The crystalline compound (I) exists in two modifications and is clearly characterised by the crystal structures of these modifications.

| Modification (A). Crystal system: tetragonal | | | |
|---|---|---|---|
| Lattice constants: | $a = 1770.70$ pm $Z = 4$, $R = 0.0617$ | | |
| | $b = 1770.70$ pm Space group: $I4_{1/a}$ | | |
| | $c = 1173.90$ pm | | |
| | $v = 3.68062* 10^9$ pm$^3$ | | |
| Atomic coordinates: | | | |
| Atom | X/a | Y/b | Z/c |
| Al | 0.43208 (15) | 0.53086 (15) | 0.03677 (24) |
| Si | 0.46778 (17) | 0.54665 (17) | −0.23654 (27) |
| N | 0.47293 (35) | 0.49777 (36) | −0.10919 (53) |
| Hl | 0.47994 (35) | 0.46073 (36) | −0.03686 (53) |
| Cl | 0.42023 (14) | 0.64831 (14) | 0.04827 (27) |
| Cl | 0.34114 (14) | 0.46419 (17) | 0.08275 (25) |
| Cl | 0.35934 (18) | 0.55843 (23) | −0.27876 (34) |
| Cl | 0.51615 (22) | 0.64793 (17) | −0.22423 (34) |
| Cl | 0.52164 (20) | 0.48518 (21) | −0.35413 (25) |

| X-ray reflexes of the crystalline powder: WL 1.54056 SR 1 1 | | | |
|---|---|---|---|
| 9.820962 | 8.9969 | 23.5 | 0.120 |
| 6.567790 | 13.4705 | 16.2 | 0.060 |
| 6.259745 | 14.1367 | 59.0 | 0.100 |
| 5.270109 | 16.8089 | 16.3 | 0.140 |
| 4.889002 | 18.1298 | 17.4 | 0.140 |
| 4.528325 | 19.5876 | 23.5 | 0.080 |

-continued

| | | | |
|---|---|---|---|
| 4.056501 | 21.8925 | 20.8 | 0.114 |
| 3.953203 | 22.4719 | 17.5 | 0.100 |
| 3.527854 | 25.2234 | 17.1 | 0.071 |
| 3.501981 | 25.4128 | 100.0 | 0.100 |
| 3.381154 | 26.3370 | 16.1 | 0.160 |
| 3.276878 | 27.1909 | 39.2 | 0.120 |
| 2.982553 | 29.9339 | 18.9 | 0.140 |
| 2.819988 | 31.7036 | 17.4 | 0.140 |
| 2.793576 | 32.0113 | 24.2 | 0.100 |
| 2.690679 | 33.2704 | 26.7 | 0.140 |
| 2.619857 | 34.1971 | 12.5 | 0.114 |
| 2.449430 | 36.6580 | 12.3 | 0.114 |
| 1.891907 | 48.0512 | 9.6 | 0.114 |
| 1.820717 | 50.0564 | 13.7 | 0.114 |

Modification (B):
Crystal system: orthorhombic
Lattice constants: a = 905.72 pm R = 0.0724 Z = 4
b = 1771.37 pm Space group: Pbca
c = 2227.04 pm
V = 3.57299* $10^9$ pm$^3$
Atomic coordinates:

| Atom | X/a | Y/b | Z/c |
|---|---|---|---|
| N1 | −0.10072 (81) | 0.30203 (46) | 0.39040 (32) |
| N2 | 0.10478 (79) | 0.19994 (46) | 0.36127 (32) |
| Al1 | −0.09731 (35) | 0.22017 (21) | 0.33498 (16) |
| Cl2 | −0.24706 (34) | 0.13823 (20) | 0.36033 (15) |
| Cl1 | −0.10256 (37) | 0.25354 (21) | 0.24455 (15) |
| Al2 | 0.09833 (35) | 0.27764 (20) | 0.42058 (16) |
| Cl3 | 0.08688 (35) | 0.23445 (21) | 0.50789 (15) |
| Cl4 | 0.25567 (35) | 0.35951 (21) | 0.40457 (17) |
| Si1 | 0.17372 (35) | 0.10916 (20) | 0.37146 (15) |
| Cl5 | 0.16414 (46) | 0.05257 (23) | 0.29505 (18) |
| Cl6 | 0.38343 (35) | 0.12011 (22) | 0.39867 (16) |
| Cl7 | 0.05914 (35) | 0.05484 (20) | 0.43377 (16) |
| Si2 | −0.15541 (35) | 0.39338 (20) | 0.37500 (15) |
| Cl8 | −0.02297 (39) | 0.43488 (20) | 0.31150 (14) |
| Cl9 | −0.14270 (39) | 0.45814 (20) | 0.44736 (15) |
| Cl10 | −0.36281 (35) | 0.39020 (22) | 0.34530 (16) |

X-ray Reflexes of the crystalline powder:
Sl 1.54056
SR 1 1

| | | | |
|---|---|---|---|
| 6.537394 | 13.5334 | 100.0 | 0.100 |
| 6.097664 | 14.5144 | 46.4 | 0.120 |
| 5.566283 | 15.9086 | 51.7 | 0.180 |
| 4.823008 | 18.3801 | 35.3 | 0.154 |
| 4.745433 | 18.6832 | 36.4 | 0.154 |
| 4.310358 | 20.5886 | 34.3 | 0.154 |
| 4.078937 | 21.7706 | 24.9 | 0.140 |
| 3.920489 | 22.6619 | 39.5 | 0.140 |
| 3.549396 | 25.0678 | 23.1 | 0.200 |
| 3.504730 | 25.3926 | 30.8 | 0.160 |
| 3.462872 | 25.7047 | 66.4 | 0.140 |
| 3.418085 | 26.0474 | 49.8 | 0.140 |
| 3.310311 | 26.9111 | 34.3 | 0.154 |
| 3.233748 | 27.5607 | 34.5 | 0.154 |
| 3.163951 | 28.1811 | 49.6 | 0.140 |
| 3.136591 | 28.4321 | 24.8 | 0.140 |
| 2.960805 | 30.1590 | 32.7 | 0.154 |
| 2.831757 | 31.5684 | 33.7 | 0.180 |
| 2.653391 | 33.7519 | 26.2 | 0.220 |
| 2.46634 | 36.3949 | 21.0 | 0.154 |

Modification A is obtained by selecting a reaction temperature of about 0° C. whereas a reaction temperature of ca. 40° C. leads to pure modification B.

For synthesising (I), the molar ratio of (A) to AlCl$_3$ is preferably adjusted to a value from 10:1 to 1:1 but the compounds (I) and (II) are always obtained together even when an excess of (A) is used. Compound (II) may be obtained pure according to the invention by heating compound (I) at temperatures of from 30 to 300° C. with the elimination of aluminium chloride. (Cl$_3$Si—NH—AlCl$_2$)$_2$→(Cl$_3$SiNH)$_2$AlCl+AlCl$_3$. Compound (II) is obtained as a white powder.

Moreover compound (II) can be synthesized by reaction of compound (A) with AlCl$_3$ in an organic solvent at temperatures of from 0° C. to 200° C.

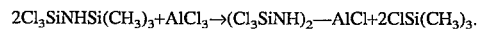

Compounds (I) and (II) thus prepared can easily be converted into an (Si—N—Al—N) ceramic powder by an ammonolysis reaction followed by pyrolysis. The ratio of silicon to aluminium in the (Si—N—Al—N) ceramic powders according to the invention can be adjusted continuously from 100:0 (pure silicon tetrachloride) to 50:50 (pure (Compound I)) by mixing the liquid compounds SiCl$_4$, HSiCl$_3$, H$_2$SiCl$_2$, and/or hexachlorodisilazane with (I) and/or (II).

Any known process of ammonolysing silicon tetrachloride may be used for the reaction with NH$_3$; this applies to the reaction with solid or liquid ammonia at low temperatures (U.S. Pat. No. 4,196,178), the reaction with gaseous ammonia in an organic solvent (U.S. Pat. No. 3,959,446) and the reaction with NH$_3$ at a high temperature with elimination of hydrogen chloride (U.S. Pat. No. 4,145,224).

After removal of the ammonium chloride by known methods such as sublimation or washing with liquid ammonia, a polymeric imide is obtained which still contains many NH or NH$_2$ groups. This polymeric imide is subsequently calcined according to the invention at temperatures of from 600° C. to 1450° C., preferably from 950° C. to 1400° C., under a stream of nitrogen. Argon, ammonia or other inert or reactive gases may be used as calcination gases as well as nitrogen.

The amorphous ceramic material prepared as described above consists of the main components Si, N and Al and may also contain traces of Cl, H, C and O. According to the invention, it has a structure consisting of (N—Si—N—Al—N) units in which both silicon and aluminium are surrounded tetrahedrally by four nitrogen atoms. Electron raster microscopic photographs confirm that completely homogeneous distribution of elements is obtained at least down to a lateral resolution of 0.5 µm. Crystallisation of the amorphous material to an Si$_3$N$_4$/AlN ceramic powder is carried out by a temperature treatment at from 1000° C. to 1750° C. According to the invention, Si$_3$N$_4$ and AlN crystallites are distributed completely homogeneously in this ceramic on a nanometer scale. The crystallite size of the primary particles is on average from 0.01 µm to 1 µm. The surface area of the powder is from 5 to 100 m$^2$/g, depending on the temperature treatment, preferably from 8 to 30 m$^2$/g.

Dense nanocomposites of Si$_3$N$_4$ and AlN are obtained by sintering this powder at temperatures of from 1450° to 1800° C. If the surfaces of the powders according to the invention are allowed to be covered with oxygen (≦10%), dense α- or β-sialon products are obtained at these temperatures, depending on the degree of oxygen covering and the sintering time. According to the invention, the enrichment with oxygen is brought about by the action of moist air at temperatures of from 20 to 200° C. over a period of from 10 minutes to 4 hours. Powders having an oxygen content of about 8% are suitable as sintering auxiliaries for sintering silicon nitride.

Monomeric or oligomeric reaction products of the formula [(NR)$_x$Cl$_y$Si—NH—Al(NR')$_x$Cl$_y$—]$_z$(x+y=5;x=3-5) in which R and R' may be identical or different and consist of C$_1$–C$_6$-alkyl, hydrogen, phenyl or vinyl may be obtained by reacting compounds (I) and (II) with primary or secondary alkylamines or aromatic amines such as methylamine, ethylamine, dimethylamine or aniline. The oligomeric units may subsequently be converted into polymers by a temperature treatment or by cross-linking with ammonia.

The consistency of the polyaluminosilazanes thus obtained ranges from slightly viscous to resinous or waxy to completely solid, depending on the groups R, R' and the degree of polymerisation.

Thermal cross-linking is carried out by the splitting off of an amine radical and the formation of linkages of new Si—N—Al—N-, Si—N—Si—N- or Al—N—Al—N- bonds. Cross-linking with ammonia is carried out by substitution of an NRR' group or an NR group by an $NH_2$ or an NH group which then undergoes further cross-linking. Both reactions may be carried out either in open systems or in closed systems (autoclave). The polymerisation temperature is from −20° C. to +300° C. and the polymerisation time is from 5 minutes to 10 days.

The invention further relates to the use of the polyaluminosilazanes according to the invention for the production of ceramic material by pyrolysis in an inert atmosphere or an atmosphere containing $NH_3$ at temperatures from 800° to 1800° C.

The ceramic yields of the pyrolyses are from 65% to 80%.

The product of pyrolysis is a ceramic material consisting to an extent of over 95% of the elements Si, Al, N and C. It may be obtained in an amorphous or a crystalline form. The crystalline phases contain $Si_3N_4$, AlN or SiC and when oxygen is present they contain α- or β-sialon. As the polyaluminosilazanes according to the invention are soluble and fusible in numerous organic solvents, they can be worked up in the form of a solution or a melt to produce suitable semi-finished products or articles such as fibres, films or coatings. The highly viscous to waxy polyaluminosilazanes may also be directly spun or moulded into suitable articles.

The articles thus obtained may be subjected before pyrolysis to a physical or chemical pretreatment (hardening, cross-linking) for the purpose of rendering the silazane resin infusible.

The invention is explained below with the aid of Examples which are not to be regarded as limiting.

EXAMPLE 1

Preparation of 1,1,1-trichloro-3,3,3-trimethyldisilazane 70 g of silicon tetrachloride (0.41 mol) and 12.5 g of hexamethyldisilazane (0.08 mol) were introduced into a 250 ml three-necked flask and stirred at room temperature for 20 hours. Subsequent fractional distillation through a short Vigreux column yielded 16.2 g (92%) of the colourless liquid 1,1,1-trichloro-3,3,3-trimethyldisilazane.

B.p. 70° C./35 torr, $^1$H-NMR (CDCl$_3$) =0.21 ppm, MS (EI) m/z=218 amu (M$^+$)

EXAMPLE 2

Preparation of μ-N,N'-bis(trichlorosilylamino)-bis-(dichloralane) (I)

22.7 g of AlCl$_3$ were introduced into 100 ml of hexane in a reaction vessel at room temperature. 38 g of Compound (I) were then rapidly added with stirring. The reaction mixture was heated to 40° C. and the AlCl$_3$ slowly reacted while the trimethyltrichlorodisilazane dissolved. After 12 hours' stirring, the reaction mixture, which had meanwhile turned into a clear solution, was cooled to room temperature and the hexane as well as the ClSi(CH$_3$)$_3$ formed during the reaction, were drawn off.

A crystalline mixture of compounds (I and II) remained behind. A mixture of 80% of compound I and 20% of compound II was obtained. Yield: 46.2 g (85% of the theory)

EXAMPLE 3

Preparation of bis(trichlorosilylamino)chloralane (III)

a) 50 g (0.1 mol) of compound (II) were subjected to a temperature treatment at about 140° C. and 0.1 mbar. The decomposition products AlCl$_3$ and compound (III) formed during this treatment were separated by fractional sublimation. 28.6 g of the crystalline compound (III) were obtained in the form of a white powder. This corresponds to a yield of 79.9% of the theory.

$^1$H-NMR: 4.15 ppm (NH); MS: 358 M$^+$ b) A mixture of 76 g (A) and 23 g AlCl$_3$ was refluxed in isooctane at a temperature of ca. 100° C. The ClSi(CH$_3$)$_3$ formed during the reaction was drawn off continuously. After 4 hours of refluxing the mixture was cooled to room temperature and the solvent was removed. 30.8 g of compound II remained behind. This corresponds to a yield of 86% of theory.

EXAMPLE 4

Ammonolysis of μ-N-bis(trichlorosilylamino)-bis-(dichloralane) (II)

200 ml (9 mol) of liquid ammonia (99.999%) were condensed in a 500 ml three-necked flask. 50 g of Compound (II) were then slowly added dropwise (1 drop/sec) with vigorous stirring at a temperature of −78° C. The suspension of imide, NH$_4$Cl and liquid ammonia then continued to be stirred for about 1 hour to dissolve as much ammonium chloride as possible in the ammonia. After removal of the residue by filtration, the latter was washed 10 to 20 times with liquid ammonia until a sample of the imide decomposed in water produced no cloudiness when silver nitrate was added.

EXAMPLE 5

Ammonolysis of a mixture of hexachlorodisilazane (Cl$_3$Si—NH—SiCl$_3$) and μ-N-bis(trichlorosilylamino)-bis(dichloralane) (II)

About 200 ml (9 mol) of liquid ammonia (99.999%) were condensed in a 500 ml three-necked flask. A mixture of 5 g of compound (II) and 57 g of hexachlorodisilazane was then slowly added dropwise (1 drop/sec) with vigorous stirring at a temperature of−78° C. This corresponds to an (Si: Al) ratio of 10:1.

The suspension of polymeric imide, NH$_4$Cl and li stirred for about 1 hour to ensure that as much ammonium chloride as possible dissolved in the ammonia. After removal of the residue by filtration, the latter was washed 10 to 20 times with liquid ammonia until a sample of the imide which had decomposed in water produced no cloudiness when silver nitrate was added.

EXAMPLE 6

Preparation of an aluminosilazane compound 100 ml of methylamine were condensed at −78° C. in an evacuated 500 ml three-necked flask equipped with a 500 ml dropping funnel but without pressure equalisation tube. 10 g (40.0 mmol of Compound (I) dissolved in 250 ml of petroleum ether were then added at such a rate with vigorous stirring that the reaction temperature did not rise above −20° C. The solid, which consisted mainly of methylamine hydrochloride, was filtered off with a reversing frit. The solvent was removed from the clear petroleum ether solution by suction filtration. A colour-less viscous oil remained behind (7 g).

$^1$H-NMR: NCH$_3$=2.0 ppm, intensity: 10; NH=0.2 ppm, intensity: 2 $^{29}$Si-NMR: δ=−38 ppm $^{13}$C-NMR: δ=27.3 ppm IR: 3320 cm$^{-1}$ (NH-stretch oscillation), 2920 cm$^{-1}$, 2800cm$^{-1}$, CH-stretch oscillation), 1550 cm$^{-1}$, 1460 cm$^{-1}$, 1050 cm$^{-1}$, 450 cm$^{-1}$

EXAMPLE 7

Preparation of a polyaluminosilazane 5 g of the oil obtained from Example 6 were heated to about 50° C. in a 50 ml flask under a protective gas. Gaseous ammonia was then passed through the liquid at a rate of 4 ml/min. A highly viscous, waxy, glass clear polymer was obtained within 2 hours. As the methylamine groups had been partly replaced by imide groups, the CH bands in the IR spectrum of this polymer were distinctly less intense than the CH bands of the compound in Example 6 whereas the intensity of the NH band increased significantly.

This polymer was subsequently pyrolysed under nitrogen at 1000° C. A black powder having a carbon content of 9.4% was obtained. The yield of ceramic material was about 70%.

EXAMPLE 8

Conversion of an imide obtained according to Example 4 or 5 into an amorphous Si—N—Al—N ceramic powder or a crystalline Si$_3$N$_4$/AlN composite powder The polymeric imide obtained as described in Example 4 was heated to 900° C. in a stream of ammonia in a tubular furnace and kept at this temperature for about 30 minutes to drive off any remaining traces of NH$_4$Cl. The material was then heated to 1200° C. at the rate of 10° C./min in a stream of nitrogen and calcined at that temperature for a further 2 hours. Since the polymeric imide was completely converted into a nitridic ceramic, the IR spectrum of the material which had thus been treated showed no NH bands. The powder obtained remained roentgeno-graphically amorphous. Conversion of the amorphous Si—N—Al—N ceramic powder into a crystalline Si$_3$N$_4$/AlN composite having AlN particles distributed microscopically uniformly in a silicon nitride matrix was carried out by 10 hours' heat treatment at 1350° C.

We claim:

1. Trichlorosilylamino-alanes corresponding to the structural formula (Cl$_3$Si—NH—AlCl$_2$)$_2$     (I)

or

Cl$_3$Si—NH—AlClNHSiCl$_3$     (II)

2. A process for the preparation of formulae of (Cl$_3$Si—NH—AlCl$_2$)$_2$     (I)

or

Cl$_3$Si—NH—AlClNHSiCl$_3$     (II)

comprising reacting 1,1,1-trichloro-3,3,3-trimethyldisilazane with AlCl$_3$ at temperatures of from about −100° C. to about 100° C. and the reaction mixture is then fractionated.

3. A process for the preparation of formula (I) according to claim 2, wherein the ratio of the reactants 1,1,1-trichloro-3,3,3-trimethyldisilazane to AlCl$_3$ is from about 10:1 to about 1:10.

4. A process as claimed in claim 3, wherein said ratio of reactants is equimolar and the reaction temperature is about 40° C.

5. A process for the preparation of formula (II) according to claim 2, wherein (Cl$_3$SiNHAlCl$_2$)$_2$ is decomposed by a temperature treatment in the range of from about 30 to about 300° C. with splitting off and removal of AlCl$_3$.

6. Aluminosilazane compounds, comprising the compounds of formulae (I) and (II) according to claim 1, wherein the chlorine atoms are partly or completely substituted by organylamino groups R, R'—N wherein R and R' may be identical or different and denote hydrogen, C$_1$–C$_6$-alkyl, phenyl or vinyl.

7. A process for the production of the alumino-silazane compound according to claim 5, wherein compounds (I) and (II) are reacted with at least 10 mol of an organylamine per mol of aluminosilazane in a solvent at temperatures of from about −80° to about 300° C.

8. Oligo- or polyaluminosilazane compounds having the structural feature ≡Si—NH—Al, comprising first coordination sphere of each silicon or aluminum atom consists only of nitrogen atoms, each nitrogen atom carrying a radical R wherein R=H, C$_1$–C$_6$-alkyl, vinyl or phenyl and n stands for a value greater than 2.

9. Oligo- or polyaluminosilazane compounds according to claim 8, obtainable by the reaction of one or both compounds —(Cl$_3$Si—NH—AlCl$_2$)$_2$ and Cl$_3$Si—NH—AlClNHSiCl$_3$ with organylamino compounds R$_2$NH or RNH$_2$ wherein R denotes C$_1$–C$_6$-alkyl, vinyl or phenyl.

10. Oligo- or polyaluminosilazane compounds according to claim 8, aluminosilazane compounds of the formula (Cl$_3$SiNHAlCl$_2$)$_2$ are obtainable by thermal polymerization or by reaction of with ammonia in open or closed systems at normal or elevated pressure and at temperatures of from about −20° C. to about 300° C.

* * * * *

UNITED STATES PATENT AND TRADEMARK OFFICE
CERTIFICATE OF CORRECTION

PATENT NO. : 5,453,527

DATED : September 26, 1995

INVENTOR(S) : Baldus, et al.

It is certified that error appears in the above-identified patent and that said Letters Patent is hereby corrected as shown below:

Item [56],
Title Page    U.S. PATENT DOCUMENTS:    Insert -- 4,767,607, 8/1988, Schleich --

Signed and Sealed this

Ninth Day of April, 1996

*Attest:*

BRUCE LEHMAN

*Attesting Officer*    *Commissioner of Patents and Trademarks*